United States Patent
Byun et al.

(10) Patent No.: US 10,568,918 B2
(45) Date of Patent: Feb. 25, 2020

(54) COMPOSITION COMPRISING CHLORELLA EXTRACT FOR PREVENTING OR TREATING LIVER DISEASE

(75) Inventors: Hee-Guk Byun, Gangwon-do (KR); Joong-Kyun Jeon, Gangwon-do (KR); Se-Kwon Kim, Busan (KR); Jung Kwon Lee, Gangwon-do (KR)

(73) Assignee: GANGNEUNG-WONGJU NATIONAL UNIVERSITY INDUSTRY ACADEMY COOPERATION GROUP (KR)

( * ) Notice: Subject to any disclaimer, the term of this patent is extended or adjusted under 35 U.S.C. 154(b) by 172 days.

(21) Appl. No.: 13/577,997

(22) PCT Filed: Nov. 25, 2011

(86) PCT No.: PCT/KR2011/009095
§ 371 (c)(1),
(2), (4) Date: Feb. 4, 2013

(87) PCT Pub. No.: WO2013/062168
PCT Pub. Date: May 2, 2013

(65) Prior Publication Data
US 2014/0308309 A1    Oct. 16, 2014

(30) Foreign Application Priority Data
Oct. 28, 2011  (KR) .......................... 10-2011-0111545

(51) Int. Cl.
| | | |
|---|---|---|
| *A61K 36/05* | (2006.01) | |
| *A61K 31/555* | (2006.01) | |
| *A61K 9/00* | (2006.01) | |
| *A23L 33/10* | (2016.01) | |
| *A23L 33/105* | (2016.01) | |
| *A23L 17/60* | (2016.01) | |

(52) U.S. Cl.
CPC .............. *A61K 36/05* (2013.01); *A23L 17/60* (2016.08); *A23L 33/10* (2016.08); *A23L 33/105* (2016.08); *A61K 9/0053* (2013.01); *A61K 31/555* (2013.01)

(58) Field of Classification Search
CPC ...................................................... A61K 36/05
See application file for complete search history.

(56) References Cited

FOREIGN PATENT DOCUMENTS

| KR | 20020031288 | * 2/2002 |
|---|---|---|
| KR | 10-354292 | 9/2002 |
| KR | 10-2004-0084376 | 10/2004 |

OTHER PUBLICATIONS

Wu et al. (2005) J. Agric. Food Chem. 53, 4207-4212.*
Lieber et al. (1975) Proc. Nat. Acad. Sci. USA vol. 72, No. 2. pp. 437-441. (Year: 1975).*
Cha et al. (2010) Journal of Agricultural and Food Chemistry 58:4756-4761 "Effect of Pressurized Liquids on Extraction of Antioxidants from *Chlorella vulgaris*".
International Search Report for PCT/KR2011/009095, dated Oct. 31, 2012, 5 pages.
Wu et al. (2005) Journal of Agricultural and Food Chemistry 53:4207-4212 "Antioxidant and Antiproliferative Activities of Spirulina and Chlorella Water Extracts".
Zakhari, Samir, Ph.D. (2006), "Overview: How is Alcohol Metabolized by the Body" Alcohol Research & Health, vol. 29, No. 4, pp. 245-254.
Riley, Thomas R., et al. (1999) "Preventive Care in Chronic Liver Disease", Journal Gen Intern Med, vol. 14:699-704.
Christensen, Erik (2010) "Glucocorticosteroids in acute alcoholic hepatitis: The evidence of a beneficial effect is getting even weaker" Journal of Hepatology, vol. 53:390-391.

* cited by examiner

*Primary Examiner* — Russell G Fiebig
(74) *Attorney, Agent, or Firm* — Adsero IP

(57) ABSTRACT

The present invention relates to a composition comprising chlorella extract for preventing or treating liver diseases. The composition comprising the chlorella extract according to the present invention may be applied to medical supplies and health supplementary food and the like, and the chlorella extract of the present invention may be usefully used as a composition for preventing or treating liver diseases because it shows inhibitory effect on liver function injury in a liver function injured model.

4 Claims, 8 Drawing Sheets

Specification includes a Sequence Listing.

H&E (X100)

Control    EtOH

EtOH + 50 CH    EtOH + 100 CH    EtOH + 10 Sul

GAPDH  NQO-1  HO-1  GR  GSTP

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence

```
<220> FEATURE:
<223> OTHER INFORMATION: Primer

<400> SEQUENCE: 1
ggcattgctc tcaatgacaa                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgtgagggag atgctcagtg                                                     20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ttctctggcc gattcagagt                                                     20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ggctgcttgg agcaaaatag                                                     20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gagcctgaat cgagcagaac                                                     20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
agccttctct ggacacctga                                                     20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
accacgagga agacgaaatg                                                     20
```

```
-continued

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggtgaccagc tcctctgaag                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggatggagac ctcacccttt                                               20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cagggccttc acgtagtcat                                               20
```

COMPOSITION COMPRISING CHLORELLA EXTRACT FOR PREVENTING OR TREATING LIVER DISEASE

CROSS-REFERENCE TO RELATED APPLICATION

This application is a 35 U.S.C. § 371 national phase application of PCT/KR2011/009095, filed on Nov. 25, 2011, entitled "Composition Comprising Chlorella Extract for Preventing or Treating Liver Disease", which application claims under 35 U.S.C. § 119(a) the benefit of Korean Patent Application No. 10-2011-0111545 filed on Oct. 28, 2011, the entire contents of which are incorporated herein by reference.

Incorporated by reference herein in its entirety is the Sequence Listing entitled "Sequences 0338.38_PCT-US_ST25," created Jun. 27, 2014, size of 3 kilobytes.

BACKGROUND (a) Technical Field

The present invention relates to a composition comprising chlorella extract for preventing or treating liver diseases.

(b) Background Art

The liver is a very important organ responsible for various metabolism, detoxification, decomposition, synthesis and secretion in a body, and specifically, its functions are as follows. First, the liver has a function of controlling energy metabolism, and it metabolizes all nutrients absorbed from foods into materials producing energy and supplies them to the entire-body or stores them. Second, the liver has functions of synthesizing, storing and distributing about 2,000 kinds of enzymes, albumin, serum proteins of clotting factors, bile acid, and lipids such as phospholipids and cholesterol. Third, the liver has a function of secreting various metabolites through a bile duct to the duodenum, and it plays an important role to sustain life due to its immune function. Finally, the liver detoxifies medicines, toxic materials, alcohols and the like due to its detoxification and decomposition functions. However, because this detoxification function of the liver damages the liver cells easily, it may induce medicine-induced, toxic or alcoholic liver diseases.

The alcoholic liver diseases may be mainly classified into alcoholic fatty liver, alcoholic hepatitis and alcoholic liver cirrhosis according to clinical symptoms, and it may be caused by drinking alcohol of 60-80 g per a day for about 10 years. The alcoholic fatty liver is caused by accumulation of cholesterol and triglycerides in liver cells by excessive alcohol drinking, and it may be recovered as soon as stop drinking, but it may develop into hepatitis by continuous drinking. The alcoholic hepatitis is a condition of generating liver cell necrosis and inflammation, and it shows various symptoms such as, tiredness, loss of appetite, weight loss, jaundice, fever, right upper quadrant pain and the like, and in about 40% of the patients having the alcoholic hepatitis, it may develop into the alcoholic liver cirrhosis. The alcoholic liver cirrhosis is a state wherein the liver can't be recovered to normal, and it shows various symptoms such as entire-body tiredness, loss of appetite, ascites, esophageal varicose vein, hemorrhage, hepatic encephalopathy, coma and the like. The prognosis is worse prognosis than the liver cirrhosis caused by hepatitis virus, and it is known that 50% of fatal cases caused by the terminal liver disease are resulted from alcohol in Europe and America.

Therefore, in order to reduce the fatality rate caused by the alcoholic liver diseases, the alcoholic fatty liver as the initial stage of the alcoholic liver diseases should be treated properly. However, up to now, proper remedies to treat the said diseases have not been developed yet.

Meanwhile, microalgae are planktons typically found in freshwater and sea water, for example, blue-green algae, diatoms, dinoflagellates, green algae, red algae, cryptomonadaceae and cryptomonads, It is estimated that more than 200,000 species exist of which about 35,000 species are described throughout the world. The microalgae, capable of performing photosynthesis like general plants and synthesizing glucides and proteins therein, are in charge of primary production in freshwater and sea water, and play an important role as a producer of the food chain.

Chlorella is a spherical single-celled plant, about 8 μm in diameter belonging to a genus of green algae such as green layer. Because the chlorella is nonsexual in reproduction, but it forms daughter cells when cell materials are increased by photosynthesis, it's reproduction is more efficient than sexual reproduction. Further, it makes organic matters by photosynthesis, and has high coefficient of utilization during photosynthesis and high protein content.

However, the clinical effect of the chlorella extract on the liver diseases as a medicine has not been disclosed yet.

Accordingly, the present inventors identified that the chlorella extract improves liver injury index so as to complete this invention.

SUMMARY OF THE DISCLOSURE

Accordingly, it is an object of the present invention to provide a composition comprising chlorella extract for preventing or treating liver diseases.

In one aspect of the present invention, provided is a pharmaceutical composition comprising chlorella extract as an active ingredient for preventing or treating liver diseases.

In another aspect of the present invention, provided is a health functional food comprising the chlorella extract as an active ingredient for preventing or improving liver diseases.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

DETAILED DESCRIPTION

Figure 1:
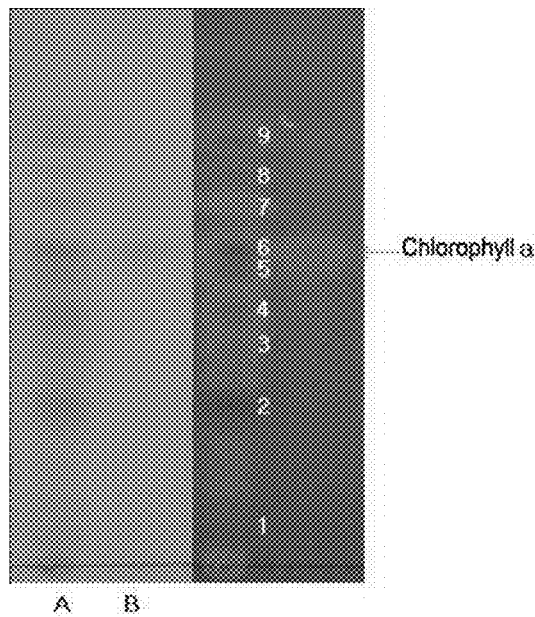
FIG. 1 is a result of isolation and purification of chlorella ethanol extract and chlorophyll a on TLC (A: chlorella ethanol extract, B: chlorophyll a)
Figure 2:
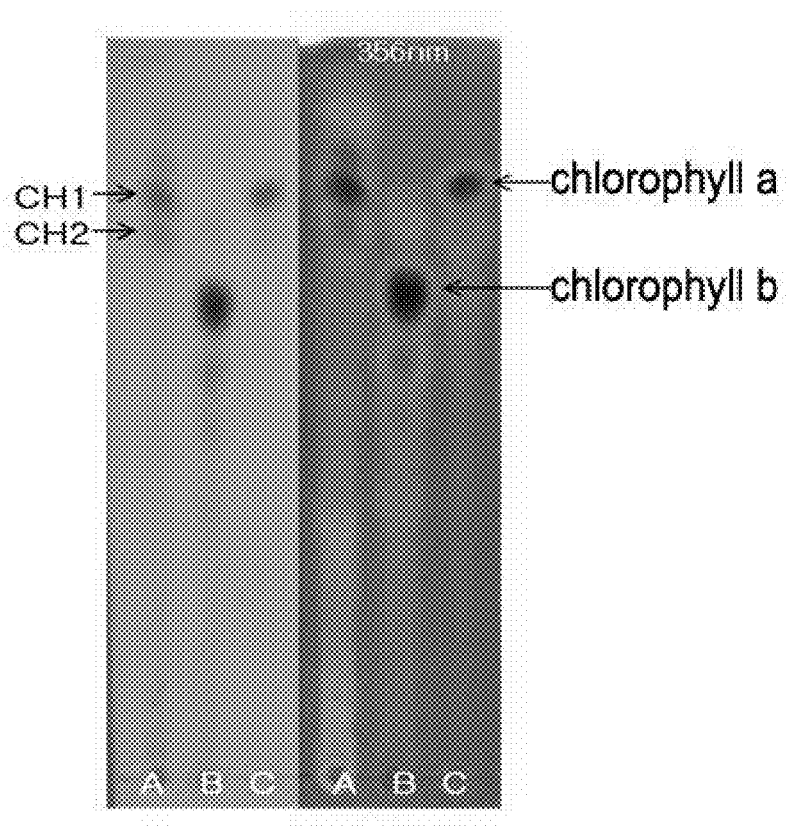
FIG. 2 is a result of isolation and purification of quinone reductase active fraction and chlorophyll a on TLC (A: quinone reductase active fraction, B: chlorophyll b, C: chlorophyll a)

Hereinafter, the preferred embodiments of the present invention will now be described in detail to enable any person skilled in the art to make and use the invention.

The present invention relates to a composition comprising chlorella extract as an active ingredient for preventing or treating liver diseases. More specifically, the present invention relates to a pharmaceutical composition comprising the chlorella extract as an active ingredient for preventing or treating the liver diseases.

The chlorella of the present invention may be a condensed freshwater chlorella, and the condensed freshwater chlorella powder may be extracted with an organic solvent to obtain the chlorella extract. More specifically, the extract may be the extract of $C_{1-4}$ alcohols, ethyl acetate or hexane, and particularly, it may be an ethanol extract.

The composition according to the present invention induces the activity of a quinone reductase, and therefore, it may show a liver function improving effect.

The liver diseases may include fatty liver, hepatitis and liver cirrhosis. In one embodiment according to the present invention, the liver function injury may have been inhibited by the composition because the liver injury indexes (ALT, AST, γ-GT and LDH) increased by liver injury are improved.

The chlorella extract may comprise chlorophyll a, and the chlorophyll a may have an effect in preventing or treating the liver diseases.

In the pharmaceutical composition of the present invention for preventing or treating liver diseases, the chlorella extract may be used at the concentration of 0.01 mg to 10 g based on the total composition.

However, the said constitution is not limited thereto, and it is changeable depending on health status of a patient, and kind and severity of diseases.

The composition comprising the extract of the present invention may further include appropriate carrier, excipient or diluent commonly used for preparing a pharmaceutical composition.

The composition comprising the extract of the present invention may be prepared into oral medicine like powder, granulum, tablet, capsule, suspension, emulsion, syrup and aerosol; external medicine; or suppository or sterile injection solution. The carrier, excipient and diluent that may be included in the composition comprising the extract of the present invention may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microchrystalline cellulose, polyvinyl pyrrolidone, water, methylhydroxybenzoate, prophylhydroxybenzoate, talc, magnesium stearate or mineral oil. When prepared into medicines, diluent or excipient such as generally used filing agents, expanders, compounding agents, humectants, disintegrators or surfactants may be added. Solid products for oral administration include tablets, pills, powder, granulum, capsules and others. The solid products may be prepared by mixing with at least one or more excipients like starch, calcium carbonate, sucrose, lactose or gelatin to the extract. Not only the simple excipient but also lubricants like magnesium stearate talc may be used. For liquid oral products, suspension, peroral liquid preparation, emulsion or syrup may be used, but commonly used simple diluents like water and liquid paraffin as well as various excipients such as humectants, sweetening agents, odorants or preservatives may also be used. Non-oral administrative products may include sterile aqueous suspension, non-aqueous solvent, suspension, emulsion, freeze-dried products or suppository. For non-aqueous solvent and suspension, propylene glycol, polyethylene glycol, vegetable oil like olive oil, or injectable ester such as ethyloleate may be used. For suppository base, witepsol, macrogol, tween 61, cacao butter, laurin fat, glycerol gelatin or others may be used.

The administration dose of the extract of the present invention may vary depending on health status and body weight of a patient, severity of disease, preparation form, pathway and period of medication, but it may be properly selected by those skilled in the art. However, for desirable effect, the extract of the present invention may be administered in single or multiple doses in the amount of 0.01 mg/kg to 10 g/Kg, preferably 1 mg/kg to 1 g/kg per day. Therefore, the above dose by no means limits the scope of the present invention.

The composition of the present invention may be administered to mammals like rat, mouse, livestock or humans through a variety of paths. For instance, it may be administered perorally, perrectum, or intravenous (IV), intramuscular (IM), subcutaneous, uterine dura mater or intracerebroventricular injection Further, the present invention relates to a health functional food comprising the chlorella extract as an active ingredient for preventing or improving liver diseases.

The chlorella extract may comprise chlorophyll a, and the chlorophyll a has a positive effect in preventing or improving liver diseases.

Further, the present invention relates to a food or food additives comprising the chlorella extract as an active ingredient having positive effects of preventing or improving liver diseases.

The composition comprising the extract of the present invention may be used in various forms of medicine, food, and beverage for preventing or improving liver diseases. The extracts of the present invention may be added to various foods like candies, beverage, gum, tea, vitamin complex, and health supplementary food, and may be used in the form of powder, granule, tablet, capsule, or drink.

The extracts of the present invention may be safely used for a long time for the purpose of prevention since they have little toxicity or adverse effect.

The extract of the present invention may be added to various food or beverage for preventing or improving liver diseases. At this time, the amount of the extracts in foods or beverages may generally be 0.01 to 15 weight % of the total food weight. For health beverage composition, 0.02 to 10 g, preferably 0.3 to 1 g, of the extract may be added to 100 ml.

For the health beverage composition, only the extract is an essential ingredient with prescribed ratio, and there are no special restrictions on the liquid ingredients. Like common beverages, various kinds of flavors and natural carbohydrate may be added. The examples of the above mentioned natural carbohydrate would be mono-saccharides, disaccharides such as glucose and fructose, polysaccharides such as maltose and sucrose, general sugar such as dextrin and cyclodextrin, and sugar alcohol such as xylitol, sorbitol, and erithritol. In addition to the above mentioned flavors, natural flavors (thaumatin, stevia extract (i.e., rebaudiosid A, glycyrrhizin)) and synthetic flavors (i.e., saccharides, aspartame) may be used. For the above natural carbohydrate composition, generally about 1 to 20 g per 100 ml of the composition of the present invention, preferably 5 to 12 g, may be used.

Other than the above, the composition of the present invention may contain various nutrients, vitamins, minerals (electrolyte), synthetic and natural flavoring agents, colorants, extenders (such as cheese, chocolate), pectic acid and pectinate, alginic acid and alginate, organic acid, protective colloid thickening agents, pH adjusting agent, stabilizer, preservatives, glycerin, alcohol, carbonator used in carbonated beverages and others. Additionally, the composition of the present invention may contain the flesh of fruits to produce natural fruit juice, fruit juice beverages, and vegetable beverages. These ingredients may be used alone or in combination. The ratios of these additives are not significant, but generally 0 to 20 weight parts per 100 weight parts of the composition of the present invention may be used.

Hereinafter, the present invention is explained by the following examples and experimental examples in more detail. The following examples are intended to further illustrate the present invention, and the scope of the present invention cannot be limited thereby in any way. The embodiments of the present invention are provided for illustration purpose only to a person having ordinary skill in the art.

EXAMPLE

Example 1

Ethanol Extraction of Condensed Freshwater Chlorella 99.9% Ethanol (Daejeong, Korea) 500 Ml was added to the powdered condensed freshwater chlorella 100 g, and stirred under dark condition. Then, the resulting mixture was extracted two times every 12 hours, and concentrated under reduced pressure to obtain an ethanol extract. Then, the activity of a quinone reductase was measured using a certain weight of the concentrated ethanol extract.

Example 2

Figure 3:
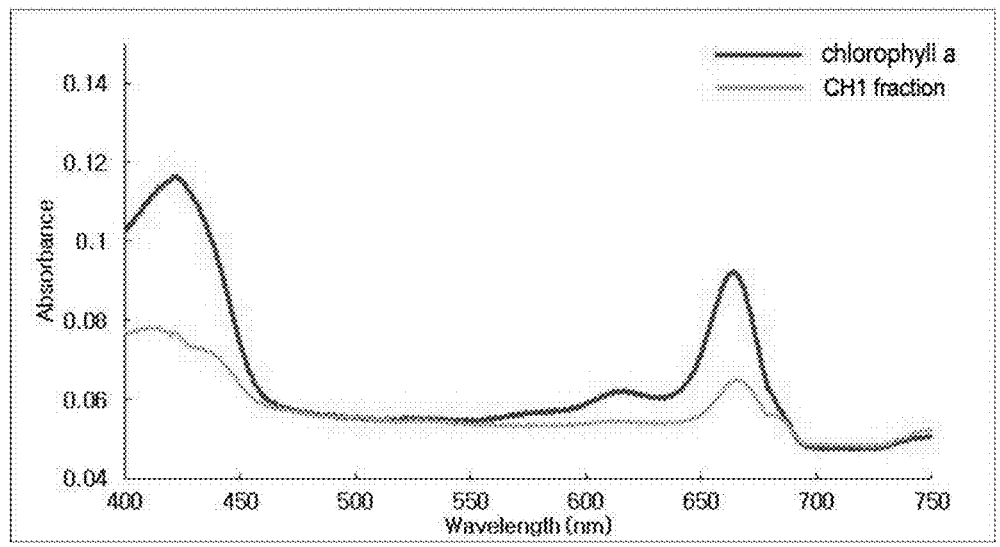
FIG. 3 is a graph showing the maximum absorption wavelength of quinone reductase active fraction (CH1) and chlorophyll a in a visible light region (400~800 nm)
Figure 4:
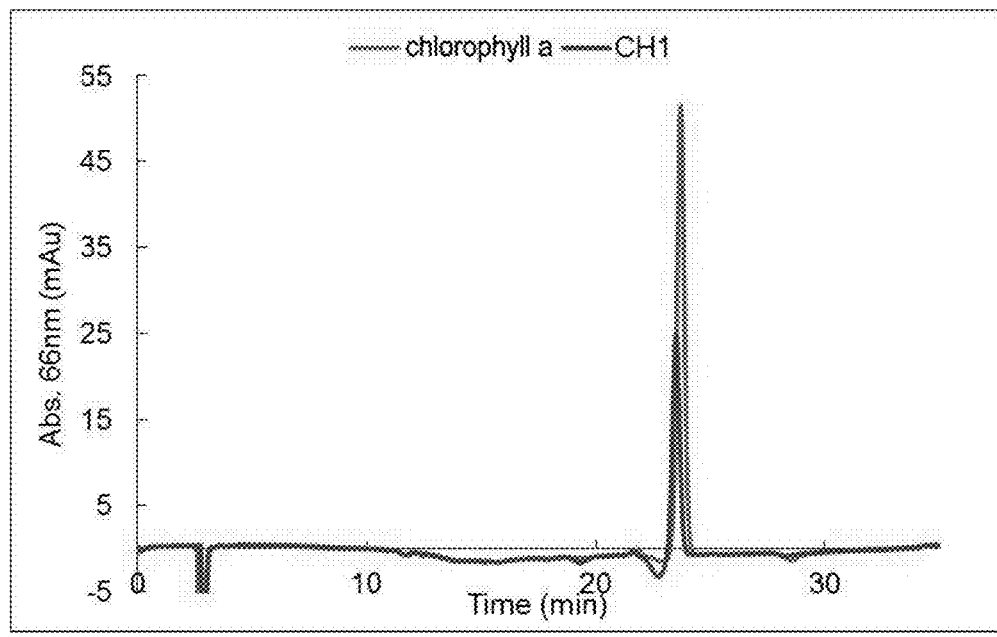
FIG. 4 is a result of isolation of chlorophyll a and chlorella ethanol extract on HPLC.
Figure 5:
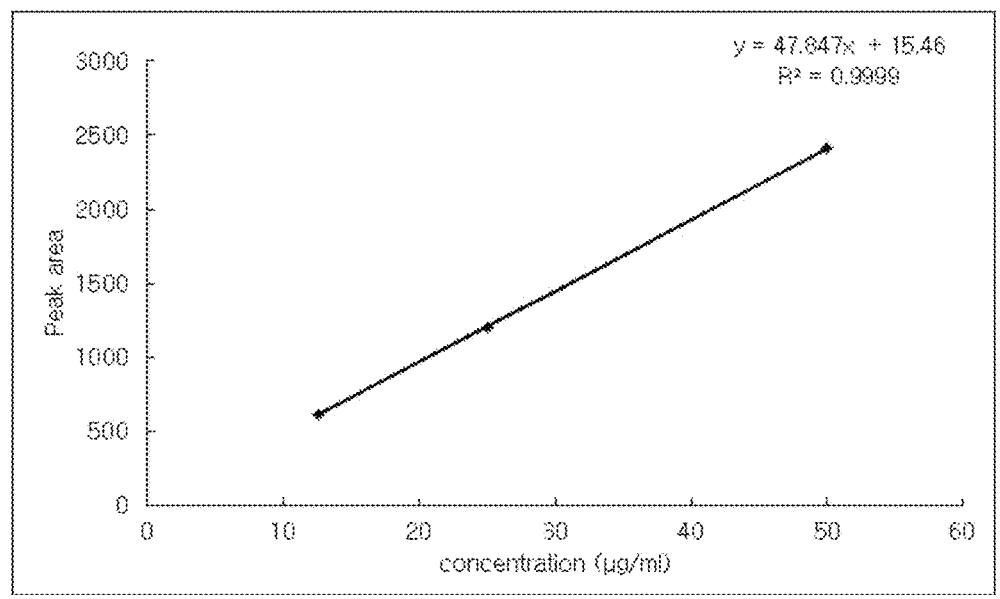
FIG. 5 is a standard curve of the chlorophyll a detected on HPLC according to its concentration.
Figure 6:
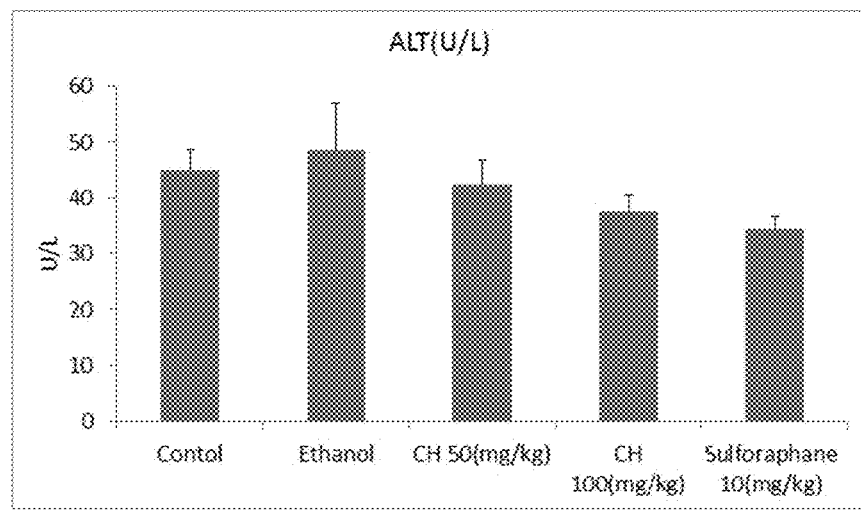
FIG. 6 is a result showing ALT (U/L) concentration in blood of liver injury-induced animal models.
Figure 7:
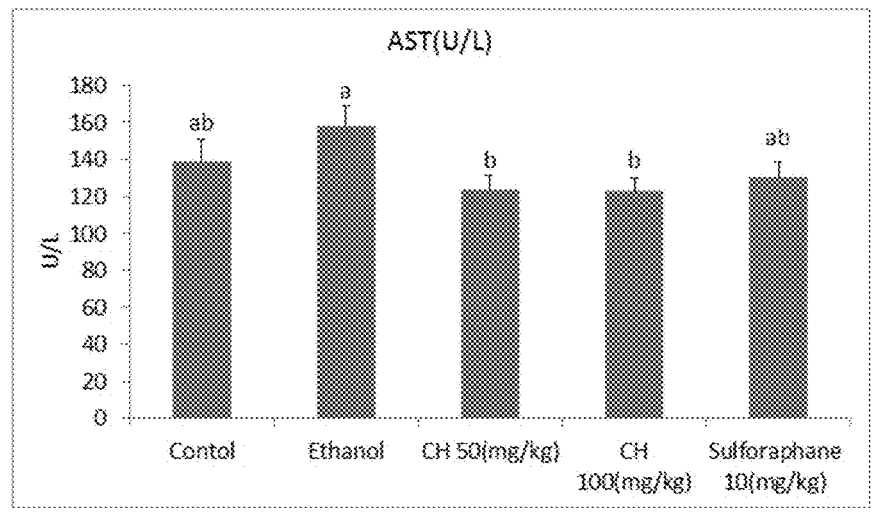
FIG. 7 is a result showing AST (U/L) concentration in blood of liver injury-induced animal models.
Figure 8:
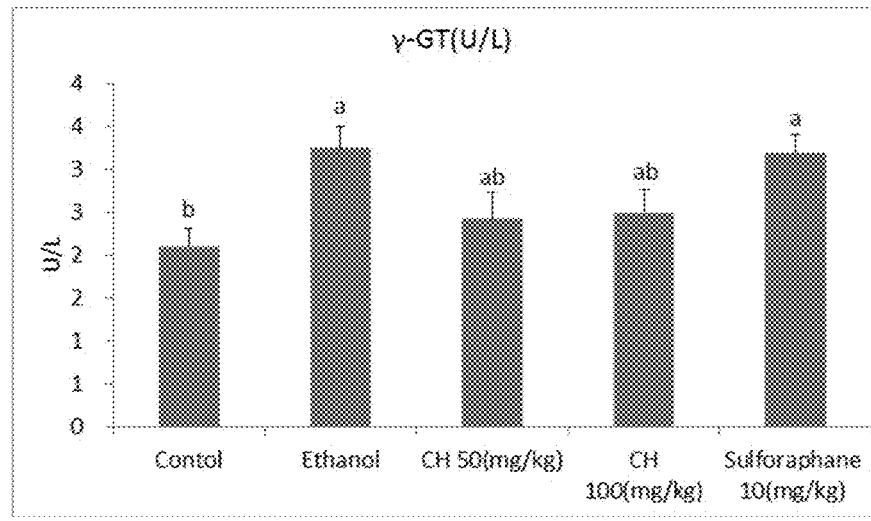
FIG. 8 is a result showing γ-GT (U/L) concentration in blood of liver injury-induced animal models.
Figure 9:
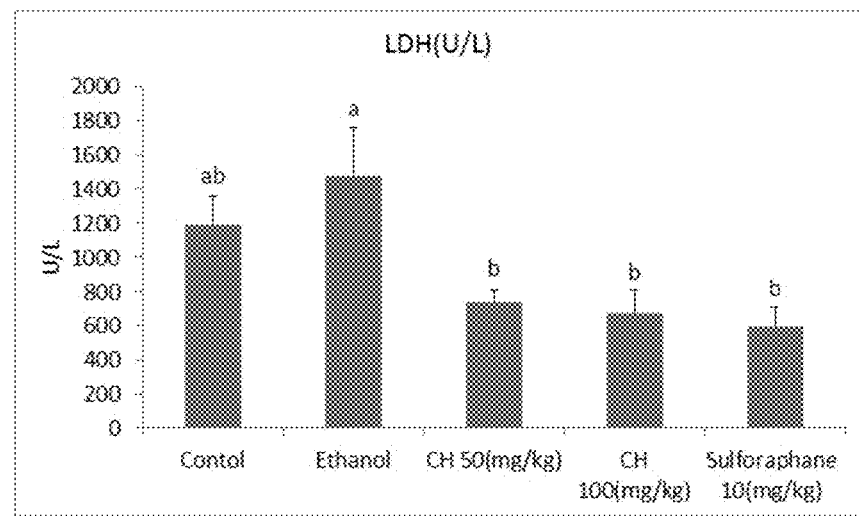
FIG. 9 is a result showing LDH (U/L) concentration in blood of liver injury-induced animal models.
Figure 10:
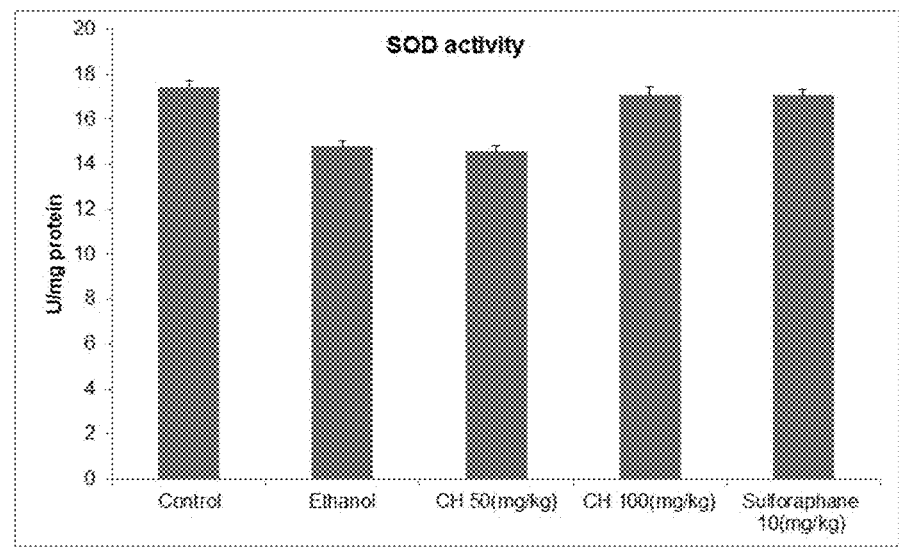
FIG. 10 is a result showing SOD activity concentration in liver cytosol of liver injury-induced animal models.
Figure 11:
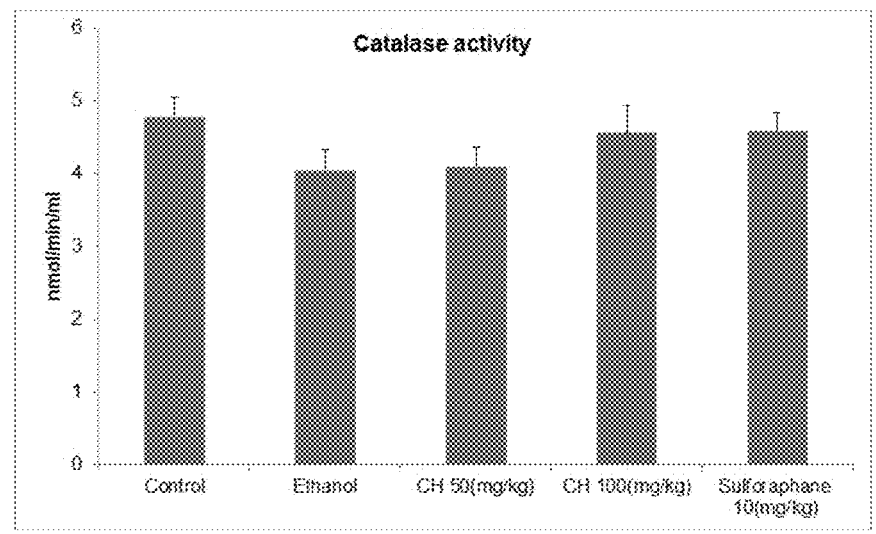
FIG. 11 is a result showing CAT activity concentration in liver cytosol of liver injury-induced animal models.
Figure 12:
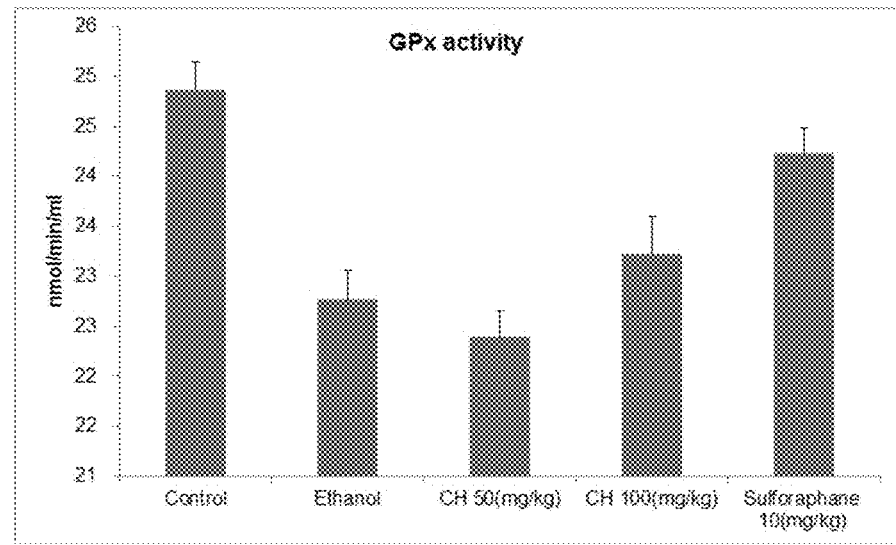
FIG. 12 is a result showing GPx activity concentration in liver cytosol of liver injury-induced animal models.
Figure 13:
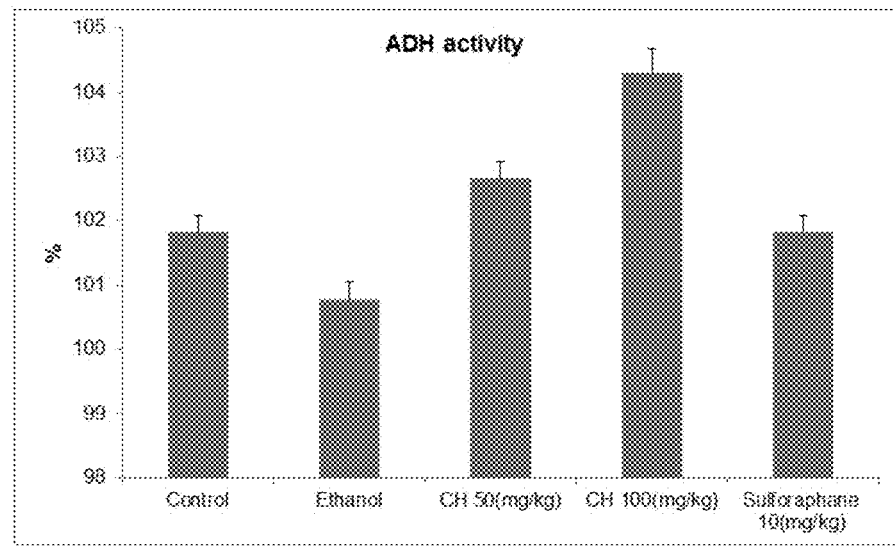
FIG. 13 is a result showing ADH activity concentration in liver cytosol of liver injury-induced animal models.
Figure 14:
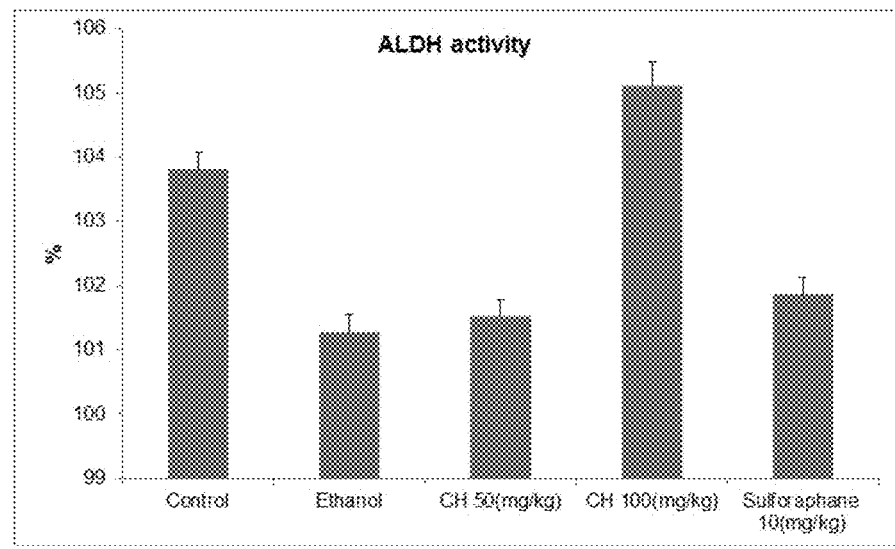
FIG. 14 is a result showing ALDH activity concentration in liver cytosol of liver injury-induced animal models.

Isolation and Purification of Material for Preventing and Treating Liver Disease from Chlorella Using Thin Layer Chromatography Ingredients of the fractions were identified using thin-layer chromatography (TLC). The chlorella ethanol extract was isolated on TLC. TLC may fractionate the organic solvent extract into non-polar and polar materials, and the chlorella ethanol extract and chlorophyll a were isolated using an eluent (hexane:ethylacetate:acetone=7:3:0.1) (FIG. 1). $R_f$ value of the chlorophyll a was 0.8. The quinone reductase activity of the isolated chlorella ethanol extract fractions were measured, and the results are listed in Table 2. As a result, the fraction having $R_f$ value of 0.8 among the chlorella ethanol extract fractions showed the highest activity. The most active chlorella ethanol extract fraction was isolated on TLC under the same condition, and as a result, the fractions having the same $R_f$ value with the chlorophyll a (CH1 and CH2) were isolated. The activity of each faction was measured and the results are shown in Table 3. The absorbances of the CH1 fraction and the chlorophyll a were detected in a visible light region (400~800 nm), and as a result, the maximum absorption wavelength of the two materials was 660 nm (FIG. 3). Further, the chlorella ethanol extract and the chlorophyll a were isolated on HPLC, and the results were compared. The analysis was conducted by eluting a solvent solution A (75:25 (v/v) methanol/water) at flow rate of 1.0 Ml/min for 30 min with 50% concentration gradient on C18 ODS column (4.6×250 mm, 5 μm). The detection wavelength was 660 nm. As a result, the same fraction with chlorophyll a was identified in the chlorella ethanol extract (FIG. 4). Further, chlorophyll a as a standard material was detected on HPLC according to its concentration, and the results are shown in FIG. 5. As a result of calculating the content of the chlorophyll a in the chlorella ethanol extract, the chlorophyll a content was 10.0±2.0% based on the extract 1 g. This means that the chlorophyll a content is 1.5±2.0% based on the dried chlorella 1 g, and the material for preventing or treating the liver diseases of the present invention is estimated to be the chlorophyll a-based material.

Example 3

Quinone Reductase Activity of Extract

For the ethanol extract and the ingredients of the isolated fractions, the quinone reductase activity induction was analyzed. In order to measure the quinone reductase activity induction effect of the fractions obtained from the chlorella, the experiment was conducted using a liver cancer cell line (Hepa1c1c7) of a white rat.

First of all, a-MEM (minimum essential medium)/10% FBS (fetal bovine serum) solution was mixed with a liver cell culture solution to make the cell number of $1\times10^5$ cells/Ml, and the resulting solution 100 μl was added to a 96-well plate followed by incubating for 24 hours under a condition of 5% $CO_2$ and 37° C. After the cells were stabilized, the compounds of the extract from the chlorella and the fractions obtained from the extract were added thereto with seven different concentrations as increased twice from 3.125 to 200 μg/Ml followed by incubating for 24 hour under a condition of 5% $CO_2$ and 37° C. After completing the incubation, the cells were washed with PBS (phosphate buffered saline) solution, and the cell membranes were lyzed with 80 μl solution containing 0.08% digitonin and 2 mM EDTA to obtain a protein solution.

The protein solution 50 μl and reaction solution A (49 Ml 25 mM Tris buffer, 34 mg BSA, 0.34 Ml 1.5% tween-20 solution, 0.34 Ml co-enzyme solution, 100 unit glucose-6-phosphate dehydrogenase, 15 mg MTT, 50 μl 50 mM menadione) 200 μl were mixed together, and the absorbance increasing rate was measure at 610 nm using a microplate reader. The protein amount was measured at 595 nm using Bradford solution. In the reaction solution A, the co-enzyme solution was made up of 150 mM glucose-6-phosphate, 4.5 mM NADP and 0.75 mM FAD, and the MTT is an abbreviation for 3-(4,5-dimethylthiazo-2-yl)-2,5-diphenyltetrazolium bromide. The quinone reductase activity of the extract and the fraction was expressed as CD (the concentration of the sample where the quinone reductase activity of the sample-treated cell becomes twice). Table 1 shows the quinone reductase activity of the ethanol extract.

TABLE 1

| Sample | Hepa1c1c7 CD (μg/Ml) |
|---|---|
| *Chlorella* ethanol | 15.65 |
| Sulforaphane (5 μM) | 1.94 |
| 5 × 10³ cell/wells | |
| Treatment Concentration 200 μg/Ml | |

As shown in Table 1, when the quinone reductase activity of the ethanol extract was expressed as CD (μg/Ml), it was 15.65. In order to identify the active material, isolation and purification were performed. By comparing ethanol extract with chlorophyll a from TLC the active fraction of quinone reductase, which has the same $R_f$ value, was confirmed.

The activity of each fraction is listed in Tables 2 and 3.
Tables 2 and 3 show the quinone reductase activities of the fractions isolated from the ethanol extract on TLC.

TABLE 2

| Sample | Hepa1c1c7 CD(μg/Ml) |
|---|---|
| 1 | 35.86 |
| 2 | 39.48 |
| 3 | 31.56 |
| 4 | 25.85 |
| 5 | 18.85 |
| 6 | 12.94 |
| 7 | 30.58 |
| 8 | 40.45 |
| Sulforaphane (5 μM) | 2.48 |
| *Chlorella* ethanol | 17.5 |
| 5 × 10³ cell/wells | |
| Treatment Concentration 200 μg/Ml | |

TABLE 3

| Sample | Hepa1c1c7 CD(μg/Ml) |
|---|---|
| CH1 | 10.85 |
| CH2 | 15.31 |
| Sulforaphane (5 μM) | 2.07 |
| Fraction 6 | 16.89 |
| 5 × 10³ cell/wells | |
| Treatment Concentration 200 μg/Ml | |

Example 4

Evaluation of Effect of Chlorella Ethanol Extract for Preventing and Treating Liver Disease in Liver-Injured Animal Model 4.1: Sample The chlorella ethanol extract (CH) was used. The CH was dissolved in ethanol, and mixed with AIN-76 diet to be a daily intake of 50 mg or 100 mg per kg of a test animal weight and supplied to the animal.

4.2: Test Animal and Feeding

Specific pathogen free male SD rats of 5-week-old were purchased from Orient Bio Inc. (Seongnam, South Korea). After inspection and adaptation for 1 week, healthy animals without weight loss were selected and used for the test. Test animals were bred under a condition of temperature: 23±3, relative humidity: 50±10%, air change rate: 10-15 times/hour, lighting time: 12 hours (08:00-20:00) and luminous intensity: 150-300 Lux. During adaptation period of 1 week, the test animals were freely fed with solid feed for test animal (Superfeed Co., Ltd., Wonju, South Korea) and drinking water. After the adaptation period of 1 week, healthy animals were selected, and divided to 5 groups by randomized block design. Namely, those were divided into a control group not treated with ethanol and the test material, a group orally administered with ethanol, a group orally administered with ethanol and fed with CH 50 mg/kg, a group orally administered with ethanol and fed with CH 100 mg/kg and a group orally administered with ethanol and fed with sulforaphane 10 mg/kg. The primary feed used in this experiment, AIN-76 was purchased from Research Diets, Inc. (New Brunswick, N.J., USA), and its composition is listed in Table 1. Test feeds were prepared by mixing each test compounds to the feed to the daily feeding amount of 50 or 100 mg per 1 kg of test animal weight as described above, and fed. In order to induce the fatty liver by ethanol, 20% ethyl alcohol 5 g per kg (body weight) was orally administered twice a day (morning and afternoon) for 16 days. The feeds containing the test compounds were fed for 10 days after $17^{th}$ day of the ethanol administration, and the ethanol was orally administered together with the feed continuously. During the test period, drinking water was freely supplied. The feed intake was measured every two days, and body weight was measured every week from the day of starting the oral administration of ethanol (0 day) to the final day of the experiment. All animal tests in the experiment were performed with the approval of hallym university experimental animal experiment ethics committe (Hallym 2010-102).

4.3: ALT, AST, γ-GT and LDH Contents in Blood Serum

To analyze contents of ALT, AST, γ-GT and LDH in a blood serum isolated from the blood collected on the day of the autopsy, alanine aminotransferase (ALT), aspartate aminotransferase (AST), gamma-glutamyl transferase (γ-GT) and lactic dehydrogenase (LDH) were analyzed using a blood biochemistry analyzer (KoneLab 20, Thermo Fisher Scientific, Waltham, Finland).

The contents of the ALT, AST, γ-GT and LDH in the blood serum are shown in FIGS. 6 to 9, respectively. The serum ALT tended to be reduced in all groups, compared with the group orally administered with ethanol. The serum AST tended to be significantly reduced in all groups, compared with the group orally administered with ethanol, and particularly, showed a great difference in the CH 50 mg/kg group and the CH 100 mg/kg group. The γ-GT increased significantly in the group orally administered with ethanol only, compared with the control group, decreased significantly in the CH 50 mg/kg group and the CH 100 mg/kg group, compared with the group orally administered with ethanol only, and did not show the significant difference in the sulforaphane 10 mg/kg group. The LDH content decreased in the CH 50 mg/kg group, the CH 100 mg/kg group and the sulforaphane 10 mg/kg group, compared with the group orally administered with ethanol with the significant difference.

4.4: SOD, CAT, GPx, ADH and ALDH Activities in Liver Cytosol 1 g liver tissue was homogenized with 0.25 M sucrose (pH 7.0). The homogenate was centrifuged at 700 rpm for 10 min and at 4,000 rpm for 10 min followed by collecting the supernatant, and then centrifuged again at 50,000 rpm for 1 hour. The supernatant was used as a cytosolic zymogen. The activities of superoxide dismutase (SOD), catalase (CAT) and glutathione peroxidase (GPx) were measured using a kit of Cayman chemical company (Ann Arbor, Mich., USA). The activity of alcohol dehydrogenase (ADH) was measured by adding 0.2 M ethanol 10 µl, 0.05 M semicarbazide HCl 10 µl and 0.1 M NAD (in 0.01 M HCl) 10 µl to 0.1 M Tris-HCl buffer (pH 8.5) 160 µl followed by adding the cytosolic zymogen 10 µl thereto at 340 nm. The activity values were expressed based on the ethanol administration group as 100%. The activity of acetaldehyde dehydrogenase (ALDH) was measured by adding 1 M KCl 10 µl, 0.1 M pyrazole 10 µl, 1 M 2-mercaptoethanol 10 µl, 0.1 M propione aldehyde 10 µl and 0.1 M NAD (in 0.01 M HCl) 10 µl to 0.2 M Tris-HCl buffer (pH 8.3) 150 µl followed by adding the cytosolic zymogen 10 µl at 340 nm, and the enzyme protein assay was conducted by a method of Lowry et al. (Lowry O H et al., 1957, J Biol Chem 193: 265-276).

The activities of SOD, CAT, GPx, ADH and ALDH in the liver cytosol are shown in FIGS. 10 to 14. The liver cytosol SOD activity increased in the CH 100 mg/kg group and the sulforaphane 10 mg/kg group, compared with the ethanol administration group, and the CAT activity increased in the CH 100 mg/kg group and the sulforaphane 10 mg/kg group, compared with the ethanol administration group but did not show the significant difference. Further, the GPx activity increased in the CH 100 mg/kg group and the sulforaphane 10 mg/kg group, compared with the group orally administered with ethanol but did not show the significant difference. The ADH activity increased significantly in the sample-treated groups, compared with the group orally administered with ethanol. The ALDH activity tended to be increased in the CH 100 mg/kg group, compared with group orally administered with ethanol.

4.5: Contents of Total Lipid, Triglyceride and Total Cholesterol in Liver Tissue Total lipid content in the liver tissue was analyzed by homogenizing 1 g liver tissue in a saline 3 ml followed by homogenizing again with CM solution (Chloroform:Methanol=2:1) 9 ml. The homogenate was centrifuged at 3,000 rpm for 10 min, and the lower layer was collected and evaporated followed by measuring the total lipid content using a precision scale. The measured total lipid was dissolved in isopropanol, and the triglyceride content and the total choresterol content were measured by a quantitative analysis kit using an enzyme method (Asan Pharm. Co., Ltd., Hwaseong, South Korea). The contents of the total lipid, the triglyceride and the total cholesterol in the liver are listed in Table 5. The total liver lipid contents were not significantly different between all groups (Table. 5). The liver triglyceride contents decreased significantly in the sample-treated groups, compared with the group orally administered with ethanol, but did not show the significant difference in all groups (Table 4). The total liver cholesterol contents decreased in the CH 50 mg/kg group and the Sulforaphane 10 mg/kg group, compared with the group orally administered with ethanol, and showed the significant difference (Table 5).

4.6: Content of Lipid Peroxide in Liver Microsome 1 g Liver tissue was homogenized in 0.25 M sucrose (pH 7.0). The homogenate was centrifuged at 700 rpm for 10 min and at 4,000 rpm for 10 min followed by collecting the supernatant, and then centrifuged at 50,000 rpm for 1 hour. The obtained precipitate was suspended in 0.25 M sucrose 10 ml again and centrifuged at 10,000×g for 15 min, and the supernatant thereof was centrifuged again at 50,000 rpm for 1 hour to obtain a precipitate. The obtained precipitate was suspended in PBS. The content of the lipid peroxide was measured by a lipid peroxide measuring kit (BioAssay Systems, Hayward, Calif., USA), and the protein quantification was conducted by a method of Lowry et al. (Lowry O H et al., 1957, J Biol Chem 193: 265-276). The lipid peroxide contents in the liver microsome are listed in Table 4. The lipid peroxide contents tended to be reduced in the CH 50 mg/kg group and the CH 100 mg/kg group, compared with the group orally administered with ethanol, but did not show the statistically significant difference (Table 4). The following Table 4 shows the contents of the total lipid, the triglyceride, the total cholesterol and the lipid peroxide in the liver.

TABLE 4

| EtOH (20% ethyl alcohol 5 g/kg) | Treatment | Total lipid (mg/g liver) | Triglyceride (mg/g liver) | Total cholesterol (mg/g liver) | Lipid peroxide (µM/mg protein) |
|---|---|---|---|---|---|
| − | − | 46.04 ± 2.72 | 13.06 ± 1.58 | 4.71 ± 0.10$^a$ | 2.02 ± 0.16 |
| + | − | 49.34 ± 1.27 | 15.08 ± 0.61 | 4.88 ± 0.0$^{9a}$ | 2.19 ± 0.09 |
| + | CH 50 (mg/kg) | 47.37 ± 1.14 | 14.07 ± 2.16 | 4.61 ± 0.12$^{ab}$ | 1.93 ± 0.23 |
| + | CH 100 (mg/kg) | 47.93 ± 1.25 | 14.82 ± 1.24 | 4.72 ± 0.09$^a$ | 1.78 ± 0.18 |
| + | Sulforaphane 10 (mg/kg) | 48.26 ± 0.99 | 13.28 ± 0.77 | 4.39 ± 0.11$^b$ | 2.07 ± 0.24 |

Values are expressed as mean ± SEM
Means with the different lettered superscripts in a same column are significantly different at the $p < 0.05$ levels by Duncan's multiple range test.

4.7: Contents of Triglyceride, Total Cholesterol and HDL-Cholesterol in Blood Serum The contents of the triglyceride, the total cholesterol and the HDL-cholesterol in the serum are listed in Table 5. The triglyceride contents tended to be reduced in all groups, compared with the group orally administered with ethanol, but did not show the significant difference (Table 5). The total serum cholesterol contents increased significantly in the group orally administered with ethanol only, compared with the control group, and decreased significantly in the CH 100 mg/kg group, compared with the group orally administered with ethanol only (Table 5). The HDL-cholesterol contents decreased in the ethanol administration group, compared with the control group. Further, when the CH was administered, the HDL-cholesterol content increased significantly, compared with the ethanol administration group (Table 5). The following Table 5 shows the contents of the triglyceride, the total cholesterol and the HDL-cholesterol in the serum.

TABLE 5

| EtOH (20% ethyl alcohol 5 g/kg) | Treatment | Triglyceride (mg/dL) | Total cholesterol (mg/dL) | HDL-cholesterol (mg/dL) |
|---|---|---|---|---|
| − | − | 130.84 ± 26.61 | 64.84 ± 5.16$^b$ | 32.72 ± 1.80$^{ab}$ |
| + | − | 136.03 ± 14.30 | 102.08 ± 7.68$^a$ | 29.77 ± 2.73$^b$ |
| + | CH 50 (mg/kg) | 126.46 ± 13.66 | 101.44 ± 5.49$^a$ | 38.30 ± 2.69$^a$ |
| + | CH 100 (mg/kg) | 101.22 ± 8.28 | 82.61 ± 5.71$^{ab}$ | 38.54 ± 2.33$^a$ |
| + | Sulforaphane 10 (mg/kg) | 126.11 ± 15.65 | 94.25 ± 7.32$^a$ | 33.39 ± 1.48$^{ab}$ |

Values are expressed as mean ± SEM
Means with the different lettered superscripts in a same column are significantly different at the $p < 0.05$ levels by Duncan's multiple range test.

4.8: Histological Analysis of Liver

After the autopsy of the control group and the test compound-treated groups, the liver was collected, washed with phosphate buffered saline and fixed with 4% paraformaldehyde (Sigma, USA). The tissue was put in a Histo Cassette (Hyunil, Korea), and treated with a automatic tissue processor (Leica, Germany), and a paraffin (Sigma, USA) block was prepared by a paraffin embedding station (Leica, Germany) followed by slicing the tissue using a tissue microtome (Leica, Germany). The section was stained by a hematoxyline and eosin staining procedure (Sigma, USA), and analyzed histologically using an optical microscope (Zeiss, Germany).

Figure 15:
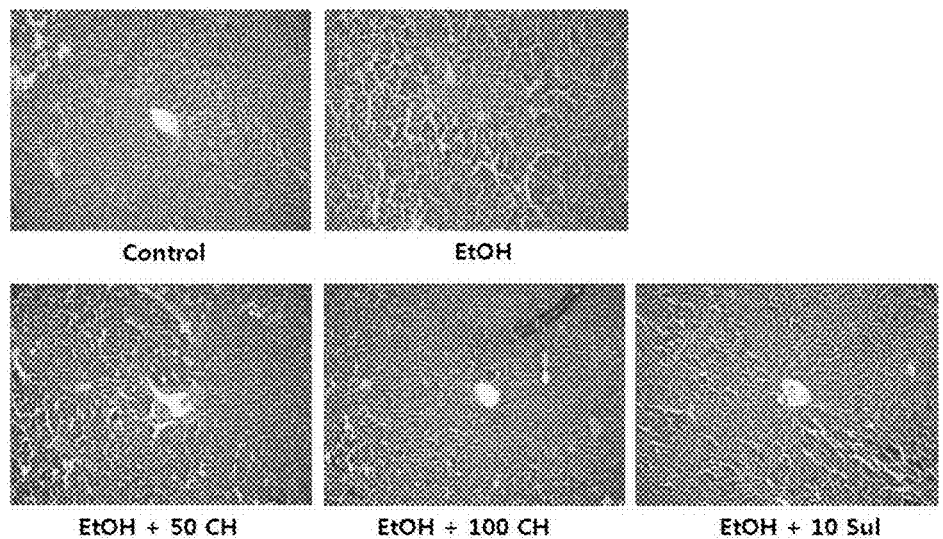
FIG. 15 is a result of histological analysis (Sul: sulforaphane) of the liver of a liver injury-induced animal model.

The hematoxyline and eosin staining of liver are shown in FIG. 15. The fatty liver and the liver injury were induced by alcohol in the group orally administered with ethanol only, compared with the control group, and the degree of the injury of the liver caused by alcohol decreased in the CH 100 mg/kg group (FIG. 15).

Example 5

Gene Expression of NQO-1, HO-1, GT and GSTP

In order to confirm the gene expressions of detoxifying enzymes acting on the liver function improvement of the chlorella ethanol extract, the degree of the gene expressions in the hepa1c1c7 cells were measured by reverse transcription polymerase chain reaction (RT-PCR). First of all, as described in Example 3, the hepa1c1c7 cells were mixed with a-MEM (minimum essential medium)/10% FBS (fetal bovine serum) solution and the solution of the cultured liver cancer cells to make the cell number to 5×10$^5$ cells/Ml, and put into a petri-dish followed by incubating for 24 hours under a condition of 5% $CO_2$ and 37. When the Hepa1c1c7 cells were grown to 80% or more of the petri-dish, chlorella ethanol extract 200 µg/Ml was added thereto. After treating the extract, the cells were incubated in a-MEM (minimum essential medium)/10% FBS (fetal bovine serum) for 24 hours under a condition of 5% $CO_2$ and 37° C. After 24 hours, RNA isolation, cDNA synthesis and RT-PCR from the cells were conducted according to the method of Komoroski et al. (Drug Metab. Dispos. 32:512-518, 2004). The gene expressions of GAPDH (glyceraldehyde phosphate dehydrogenas), NQO-1 (NAD(P)H quinone oxidoreductase), HO-1 (heme oxygenase-1), GR (Glutathione reductase), GSTP (glutathione S-transferase Pi) were confirmed by RT-PCR.

Primer sequences of each gene are listed in Table 6. cDNA was synthesized by mixing the extracted RNA as a template, oligo dT-adaptor primer and DEPC water to the total volume of 15 µL, denaturing at 70 for 5 min and performing reverse transcription of moloney murine leukemia virus (M-MLV) RNA at 42 for 60 min and at 94 for 5 min. The synthesized cDNA was amplified by PCR, and the total volume of the reaction solution was 25 µL. The final concentration of each reactant was: 100 pmol primer, 1.0 µM dNTP mixture, 0.2 mM 5×green or coloreless GoTaq Reaction buffer, 1×1.5 mM, $MgCl_2$ (PCR buffer) and GoTaq DNA polymerase 1.25 units. PCR conditions about denaturation, annealing and extension were as follows: 95 for 2 min, 95 for 30 sec, 60 for 30 sec, 72 for 1 min, 72 for 5 min and 30~40 cycles. After completing the PCR, 10 µL of each product was electrophoresed in an 2% agarose gel. After completing the electrophoresis, the gel was stained with EtBr, and the picture thereof was taken under UV using DC120 zoom digital camera (Eastman Kodak, New Haven, Conn., USA). The degree of the expression was judged based on the GAPDH expression. The following Table 6 shows the primer sequences for the liver detoxifying enzyme genes.

TABLE 6

| Primer Name | Sequence | | |
|---|---|---|---|
| GAPDH | Forward: | GGCATTGCTCTCAATGACAA | (SEQ ID NO: 1) |
| | Reverse: | TGTGAGGGAGATGCTCAGTG | (SEQ ID NO: 2) |
| NQO-1 | Forward: | TTCTCTGGCCGATTCAGAGT | (SEQ ID NO: 3) |
| | Reverse: | GGCTGCTTGGAGCAAAATAG | (SEQ ID NO: 4) |
| HO-1 | Forward: | GAGCCTGAATCGAGCAGAAC | (SEQ ID NO: 5) |
| | Reverse: | AGCCTTCTCTGGACACCTGA | (SEQ ID NO: 6) |
| GR | Forward: | ACCACGAGGAAGACGAAATG | (SEQ ID NO: 7) |
| | Reverse: | GGTGACCAGCTCCTCTGAAG | (SEQ ID NO: 8) |
| GSTP | Forward: | GGATGGAGACCTCACCCTTT | (SEQ ID NO: 9) |
| | Reverse: | CAGGGCCTTCACGTAGTCAT | (SEQ ID NO: 10) |

Figure 16:
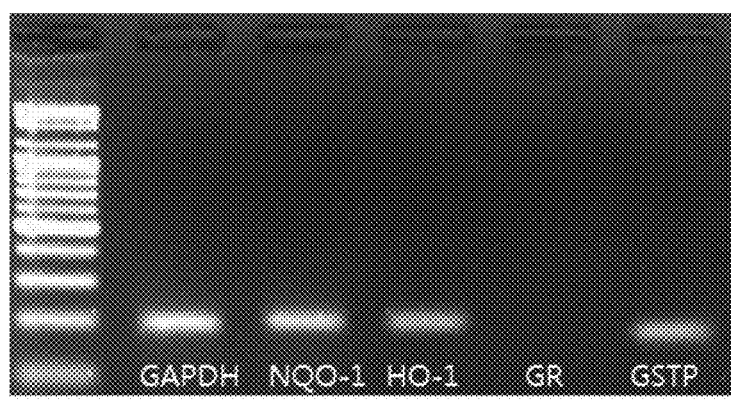
FIG. 16 is a result of gene expressions of liver detoxification enzymes and anti-oxidative enzymes, NQO-1, HO-1, GT and GSTP.

As a result of RT-PCR shown in FIG. 16, when the PCR was performed after 24 hours of the treatment, the genes of the detoxifying enzyme, NQO-1 and HO-1, and the gene of the anti-oxidant enzyme, GSTP, were expressed, but the gene of the anti-oxidant enzyme, GR, was not expressed.

According to the results of Examples 1 to 5, it was confirmed that the chlorella extract improved the activity of the quinone reductase as a detoxifying enzyme in the liver cancer cell, hepa1c1c7; and the liver injury protecting effect and the activities of the liver detoxifying enzyme and anti-oxidant enzyme in the liver-injured animal model. Therefore, it is expected that the extract may show excellent effect as a liver function improving agent, and a preventing agent and a treating agent for the liver disease in the future.

The composition comprising the chlorella extract according to the present invention may be used to a medicine and a health supplementary food and the like, and may show the liver-injury inhibiting effect in the liver-injured model. Therefore, the chlorella extract of the present invention may be usefully used as a composition for preventing and treating the liver injury.

While certain embodiments have been described, these embodiments have been presented by way of example only, and are not intended to limit the scope of the disclosures. Further, it will be apparent to those skilled in the art that modifications and variations not exemplified above can be made in the scope not departing from essential properties. For example, each component shown in detail in the embodiments may be modified and implemented. In addition, it should be understood that difference associated with the modification and application are included in the scope of the present invention defined in the appended claims.

What is claimed is:

1. A method for treating alcoholic fatty liver in a patient, comprising administering to a patient in need thereof an effective amount of a pharmaceutical composition comprising an effective dosage of chlorella extract,
   wherein the chlorella extract is an ethanolic extract which comprises chlorophyll a, and
   wherein the dosage amount of the chlorella extract is 50 mg to 100 mg per kg body weight of the subject per day.

2. The method of claim 1, wherein the composition induces quinone reductase activity.

3. A method for treating alcoholic fatty liver in a patient, comprising administering to a patient in need thereof an effective amount of a health functional food composition comprising an effective dosage of chlorella extract,
   wherein the chlorella extract is an ethanolic extract which comprises chlorophyll a, and
   wherein the dosage amount of the chlorella extract is 50 mg to 100 mg per kg body weight of the subject per day.

4. The method of claim 3, wherein the health functional food is in the form of a powder, granule, tablet, capsule or beverage.

* * * * *